(12) United States Patent
Wadsworth

(10) Patent No.: US 6,728,974 B2
(45) Date of Patent: May 4, 2004

(54) SAFETY GOGGLES WITH EARPLUGS

(76) Inventor: Jake Wadsworth, 20 Dublin Gulch Rd., St. Ignatius, MT (US) 59865

( * ) Notice: Subject to any disclaimer, the term of this patent is extended or adjusted under 35 U.S.C. 154(b) by 0 days.

(21) Appl. No.: 10/266,137

(22) Filed: Oct. 8, 2002

(65) Prior Publication Data

US 2003/0070210 A1 Apr. 17, 2003

Related U.S. Application Data

(60) Provisional application No. 60/323,341, filed on Oct. 12, 2001.

(51) Int. Cl.[7] .................................................. A41D 13/12
(52) U.S. Cl. ............................ 2/456; 128/864; 351/123
(58) Field of Search ................................ 2/9, 10, 12, 13, 2/171, 209, 423, 426, 448, 456, DIG. 11; 128/857, 858, 864; 181/130; 351/41, 123, 156, 157, 158; 455/343, 344, 347, 350, 351

(56) References Cited

U.S. PATENT DOCUMENTS

| | | | | |
|---|---|---|---|---|
| 3,856,007 A | * | 12/1974 | Leight | 128/152 |
| 5,133,596 A | * | 7/1992 | Korny et al. | 351/158 |
| 5,475,449 A | * | 12/1995 | Pyle | 351/123 |
| 5,781,272 A | * | 7/1998 | Bright et al. | 351/123 |
| 5,809,574 A | * | 9/1998 | Falco et al. | 2/209 |
| 6,082,855 A | * | 7/2000 | Fleming | 351/123 |
| 6,382,213 B1 | * | 5/2002 | Sanpei | 128/864 |

* cited by examiner

Primary Examiner—Gary L. Welch
(74) Attorney, Agent, or Firm—Keith S. Bergman

(57) ABSTRACT

An eyes and ears protection device provides a forehead beam supporting a depending goggle-like eyes shield and laterally opposed depending side shields. The lateral portions of the forehead beam pivotally support rearwardly extending temple beams, the rearward portions of which each movably interconnect a rearwardly extending ear beam by a ball and socket joint. The rearward portion of each ear beam movably interconnects an earplug structure by a ball and socket joint. Each earplug structure movably supports an earplug positionable for use in a user's auditory canal and for storage in a cavity or space defined by the ear beam.

8 Claims, 3 Drawing Sheets

SAFETY GOGGLES WITH EARPLUGS

RELATED APPLICATIONS

This is a continuation in part of provisional application No. 60/323,341 filed Oct. 12, 2001.

BACKGROUND OF INVENTION

1. Field of Invention

The invention relates generally to goggle type safety glasses and more particularly to such glasses that are of a compound adjustable nature and have ear-bow structures carrying earplugs for adjustable positioning.

2. Background and Description of Prior Art

Worker safety devices have become increasingly important in the modern work place to such an extent that in various work environments the use of some safety devices is required by statute and ancillary rules or regulations relating thereto. Safety glasses and earplugs have long been known to protect worker sight and hearing and through their course of development each device has become increasingly sophisticated. Because of the close physical association of the visual and auditory sense organs, various safety devices combining both safety glasses and earplugs in a unitary, or at least interconnected, structure have heretofore become known. Notwithstanding the sophistication of the development of these protective devices, both individually and in combination, problems still remain with them and their use. The instant invention seeks to resolve various of these remaining problems by providing a compound structure combining both safety glasses and earplugs in a new unitary assemblage.

The combined glasses and earplug assemblages that have heretofore become known have shown the benefits and advantages of having both safety devices in a single interconnected structure, but in general prior assemblages have associated these two protective devices in a fashion that has not taken advantage of the synergistic relationship each assemblage may have in a rigid articular structure that aids positional maintenance of the combined assemblage on the head of a user. Various prior combined assemblages have concentrated on the positional maintenance of one or the other of the individual protective devices, but have not accomplished this result in a fashion that is convenient and comfortable for the user nor of maximum utility for the simultaneous use of both protective elements.

One group of combined eye and ear protective devices have associated the ear protectors with eye glasses type eye protectors by interconnecting the elements with a flexible cord. With this type of interconnection neither protector aids the proper positional maintenance of the other and in some instances the interconnection may be disruptive of the positional maintenance of one or both protective devices. Other assemblages that have provided interconnection of the two safety devices by rigid articulating elements have not allowed all necessary or convenient motions of either or both safety devices to allow proper positioning and comfortable use. Prior assemblages also have not provided a reasonable amount of potential adjustment to accommodate various anatomically different features of different users to allow comfortable positioning and use of the same sized and configured protective device by reasonably large classes of users sufficient in size to make the assemblage economically viable.

In contradistinction to the known assemblages of ear and eye protectors that are articularly interconnected, the instant device provides not only articular joinder of the protectors, but also provides further articular joinder of the elements of the protectors. The instant assemblage provides a goggle type eye shield carried by a forehead beam that articularly interconnects two rearwardly extending temple beams at each lateral end for pivotal motion in a substantially horizontal plane. The rearward end portion of each temple beam provides one element of a ball and socket joint that articularly interconnects the other element of the ball and socket joint carried by an ear beam for universal motion of the elements in two mutually perpendicular planes. The ear beam in turn in its rearward end portion articularly interconnects an earplug structure, extending laterally inwardly toward the user's ears, by means of a ball and socket joint which allows earplug structure motion in two mutually perpendicular planes. Single ball and socket joints allowing two dimensional motion of ear plugs relative to supporting glasses or glasses-like supports have heretofore been known, but it does not appear that two such joints between the protective eye glasses or glasses-like ear plug supports have been known.

The instant assemblage allows necessary and desired motions for comfortable habitually familiar use of both the compound eye protector and ear protector by persons having a substantial range of face and cranial structures of differing dimensions and configurations while yet allowing use of known modern sophisticated configurations and structures for such protection devices to provide a protection device assemblage that is simple of manufacture from modern polymeric materials by known processes while yet maintaining cost within a range of economically viable.

My invention lies not in any one of these features individually, but rather in the synergistic combination of all of its structures that give rise to the functions necessarily flowing therefrom.

SUMMARY OF INVENTION

My protection device provides goggle type safety glasses having a forehead beam supporting a depending goggle-like eye shield and rearwardly extending temple beam connectors at each lateral end. Each temple beam connector pivotally interconnects a rearwardly extending temple beam for motion in a substantially horizontal plane. The rearward portion of each temple beam provides one element of a ball and socket joint to support a mating element of a rearwardly extending ear beam for motion in two mutually perpendicular planes. Each ear beam in its rearward end portion provides one element of a ball and socket joint to support the mating element of the joint carried by an earplug structure extending laterally inwardly toward a user's head for pivotal motion in two mutually perpendicular planes. Each earplug structure provides an earplug that may be positioned for use in a user's auditory canal and for storage in a cavity defined in the ear beam. The protection device is formed of elements that are resiliently deformable, but sufficiently rigid to be configurationally sustaining, such as of polymeric material.

In creating such a device it is:

A principal object to provide a single protection device that embodies both eye glasses and earplugs.

A further object is to provide such a protection device that is of a compound articulating nature for adjustable positioning of the protector elements relative to each other to allow substantially the same adjustability of the protector elements of the device as either known eye protectors or ear protectors would have individually.

A further object is to provide such a protection device that has a goggle-type eye protector carrying earplug structures on ear beams at each end of temple beams with two ball and socket joints between the forehead beam of the eye protector and each earplug structure.

A further object is to provide such a protection device that carries earplugs at the end portion of each ear beam so that the earplugs may be moved for use in a wearer's ears and for storage in a cavity defined in each ear beam.

A still further object is to provide such a protection device that is somewhat resiliently deformable with a repentant memory but yet sufficiently rigid so as to be configurationally sustaining to allow simple and economic formation from polymeric materials by known manufacturing processes.

A still further object is to provide such a protective device that is of new and novel design, of rugged and durable nature, of simple and economic manufacture and one otherwise well suited to the use and purposes in which it is intended.

Other and further objects of my invention will appear from the following specification and accompanying drawings which form a part hereof. In carrying out the objects of my invention, however, it is to be understood that its essential features are susceptible of change in design and structural arrangement with only one preferred and practical embodiment of its best known mode being illustrated in the accompanying drawings and specified as is required.

BRIEF DESCRIPTION OF DRAWINGS

In the accompanying drawings which form a part hereof and wherein like numbers of reference refer to similar parts throughout.

DESCRIPTION OF THE PREFERRED EMBODIMENT

Figure 1:
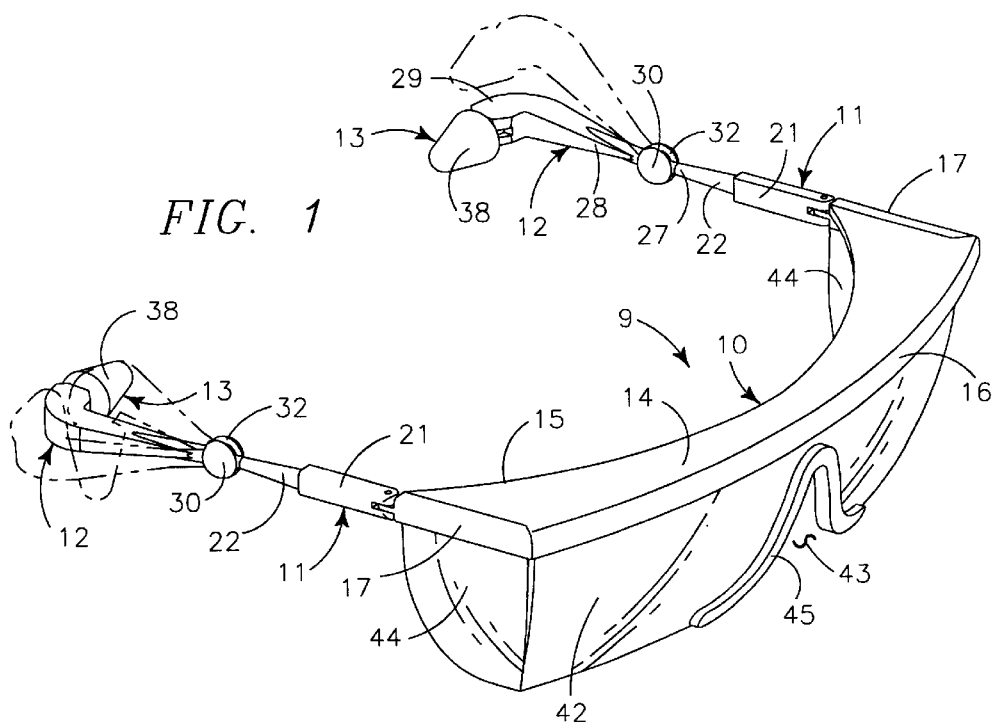
FIG. 1 is a rearwardly looking isometric view of the protection device with ear beams and earplugs shown in alternate positions in phantom outline.
Figure 2:
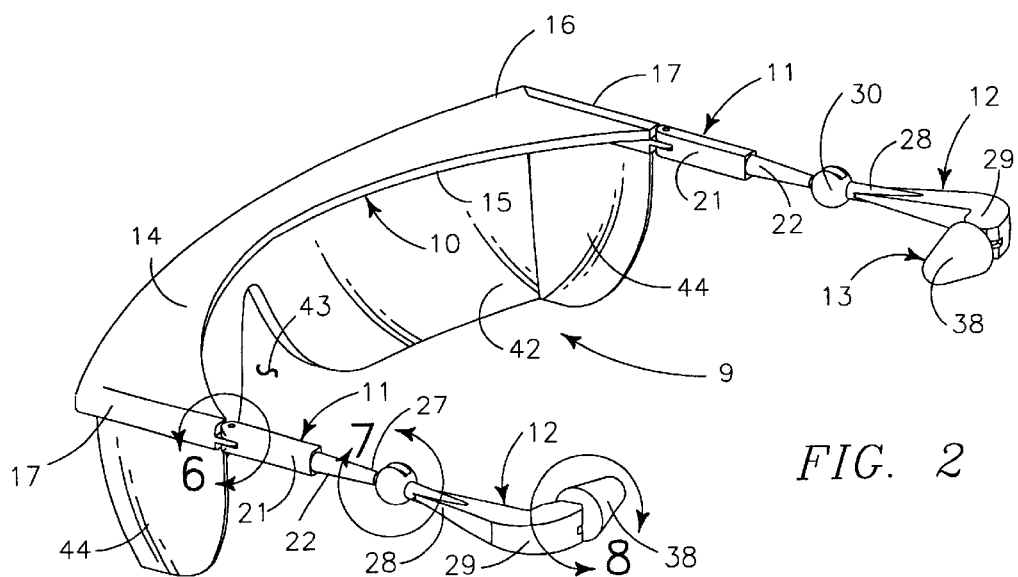
FIG. 2 is a forward looking isometric view of the protection device of FIG. 1 showing its various elements, their configuration and relationship from this aspect.

Safety glasses 9 are formed by forehead beam 10 pivotally supporting rearwardly extending temple beams 11 at each lateral end portion. Each temple beam articularly supports ear beam 12 extending rearwardly therefrom and each ear beam in its rearward portion articularly supports earplug structure 13.

Forehead beam 10, in the instance illustrated, provides flat planar body 14 having arcuate rearward edge 15 and arcuate forward edge 16 of somewhat less curvature. The rearward arcuate edge 15 preferably is defined with a configuration such as to fit in close proximity to the forehead of a user when the safety glasses are operatively positioned on the user. The curvature of forward edge 16 is not critical but preferably for habitually familiar use and optical effect is such as to maintain depending curved goggle type lens at an approximately evenly spaced distance from the face of a user at the horizontal level of the user's eyes. The lateral ends 17 of forehead beam body 14 are substantially parallel in the instance illustrated and are spaced at a distance such that when the temple beams 11 and ear beams 12 extend rearwardly in linear parallel orientation, each ear beam will pass in the space between the user's temple and the laterally outward earlobe. Within limits this dimensioning is not critical because of the adjustability of the safety glasses 9.

Figure 6:
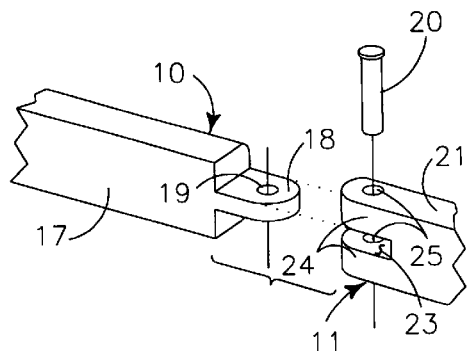
FIG. 6 is an enlarged and exploded isometric view of the joint between a temple beam connector and a temple beam, taken as in circle 6 on FIG. 2.

The rearward portion of each lateral end 17 of the forehead beam 10 defines rearwardly extending tenon 18, as seen in FIG. 6, to aid pivotal interconnection of the temple beam 11. This tenon 18 defines medial hole 19 to accept pivot pin 20 in a pivotal fit.

The safety glasses 9, in the instance illustrated, provide a goggle-like protective structure with arcuate forward eyes protector 42, defining upwardly extending nose indentation 43, depending from the forward portion of body 14 of forehead beam 10. The size and shape of the eye protector 42 is similar to that of commercial goggle type eye protectors of present day commerce and not a part of my invention per se. Similar opposed side eye protectors 44 depend from the lateral ends 17 of body 14 and communicate in their forward edge portions with the lateral edges of eyes protector 42. The side protectors 44 extend rearwardly only to the forward edge of tenon 18 to avoid interference with the joint that that tenon partially forms. Preferably nose band 45 is provided about the periphery of nose indentation 43 and the lower adjacent portion of the eye protector to provide an edge of somewhat greater area to rest and be supported on the nose structure of the user greater user comfort.

Temple beam 11 is an elongate semi-rigid structure extending rearwardly from the forehead beam 10 to a point approximately equidistant between the rearward portion of the forehead beam 10 and the head of a user perpendicularly above the auditory canal. In the instance illustrated forward portion 21 of the temple beam 11 is of somewhat rectilinear cross-section and rearward portion 22 is configured as a truncated rearwardly extending cone. The forward end of forward portion 21 defines mortise 23 to pivotally receive tenon 18 of the forehead beam 10 between forwardly extending ears 24 defined by mortise 23. Each temple beam ear 24 defines axially aligned medial hole 25 positioned to cooperatively receive and positionally maintain pivot pin 20 therein when that pivot pin is carried in hole 19 of tenon 18 of the forehead beam.

Figure 7:
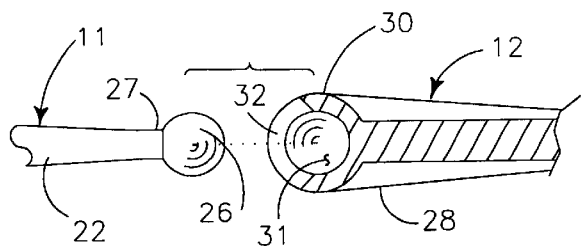
FIG. 7 is an enlarged and exploded cut away partial orthographic view of the ball and socket joint between a temple beam and associated ear beam, taken as in circle 7 on FIG. 2.

Rearward portion 22 of the temple beam 11 defines spherical ball 26, as seen in FIG. 7, to form a portion of a ball and socket joint joining the temple beam 11 and ear beam 12. Preferably the rearward part 27 of rearward portion 22 is relatively small in cross-section and not more than one half the diameter of spherical ball 26 to allow a substantial amount of angular motion of the interconnected elements of the ball and socket joint.

Ear beam 12 is a somewhat L-shaped element having forward cross-sectionally smaller elongate portion 28 and cross-sectionally larger inwardly extending lateral portion 29. The forward end of elongate portion 28 defines bulbous enlargement 30 of sufficient size to define spherical chamber 31 to movably receive ball 26 of the temple beam 11 to form a ball and socket joint. The bulbous enlargement 30 defines forwardly extending, vertically oriented slot 32 communicating therethrough to allow passage of the rearward part 27 of rearward portion 22 of temple beam 11 therein. Slot 32 does not need angular extension of more than about 180 degrees to accomplish all angular motions that may be required of it and allow placement and removal of ball 26 in and from chamber 31 by reason of the resilient deformability of the elements involved.

Figure 8:
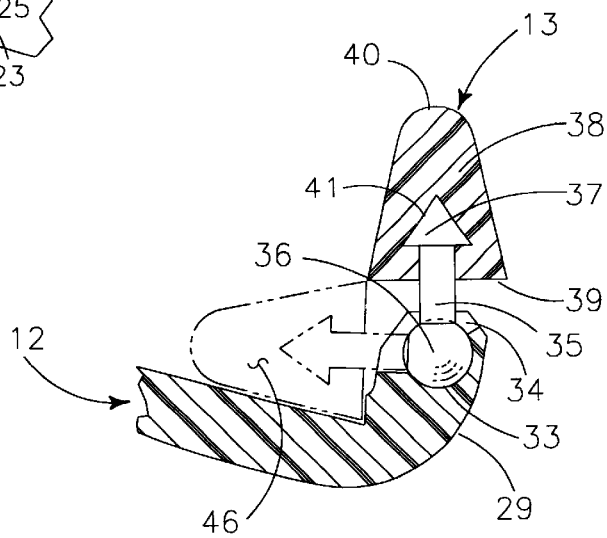
FIG. 8 is an enlarged medial cross-sectional view through the ball and socket joint between an ear beam and the associated earplug, taken as in circle 8 on FIG. 2.

The rearward lateral portion 29 of the ear beam 12 has sufficient size to allow definition of the socket portion of a ball and socket joint therein as shown in detail in FIG. 8. Spherical socket cavity 33 is formed in the end part of lateral portion 29, spacedly inwardly from the lateral end. Slot 34 is defined in lateral portion 29 to communicate from the spherical socket cavity 33 therethrough to allow passage of a shaft of a ball connector that forms a mating portion of the ball and socket joint and to allow the establishment of a ball in socket cavity 33. The slot 34 preferably communicates with cavity 33 over an angle of substantially 180 degrees so that ball 36 can be placed in cavity 33 by reason of the resilient deformability and one placed the ball will be positionally maintained in the cavity 33 by reason of the retentive memory of the materials. The slot 34 may be enlarged laterally to allow greater joint motion so long as the removed spherical surface is less than a 180 degree spherical segment.

In the instance illustrated, the ear beam 12 defines a peripheral area 46 within which an associated earplug may be stored when in a forwardly extending elongate position such as shown in phantom outline in FIG. 8. This structure is within the ambit and scope of my invention though not necessary to its functioning.

Figure 8A:
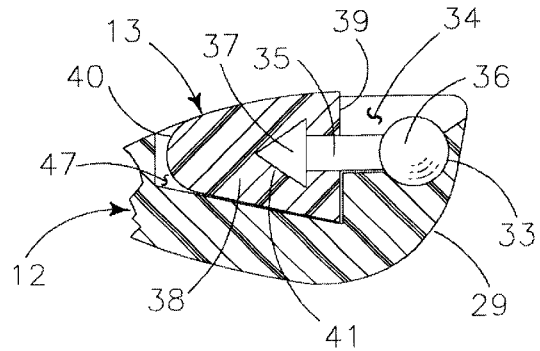
FIG. 8A is a view, similar to FIG. 8, of a species of ear beam defining a cavity for containment of the associated ear plug.

As seen in FIG. 8A, if lateral portion 29 of the ear beam 12 is of sufficient size, external opening cavity 47 may be defined in lateral portion 29 to receive and contain ear plug 38. This modified structure has the benefit of also serving as somewhat more of an ear bow than the ear plug itself if a user desires to use only the safety glasses and not the ear plugs. Again this structure is not a necessary part of my invention though it adds to the utility of the invention.

Earplug structure 13 provides earplug mounting arm 35 defining in its laterally outer end spherical ball 36 configured to movably fit in spherical cavity 33 of the ear beam 12 to form a ball and socket joint. The earplug mounting arm 35 is a cylindrical structure sized to movably fit within slot 34 of the lateral portion 29 of ear beam 12. The slot 34 preferably includes a circular segment of substantially 180° to allow all desirable motion of the mounting arm 35 therein while still allowing assemblage of the joint and positional maintenance of the ball 36 therein. The laterally inner end of mounting arm 35 defines conic fastening element 37 having an adjacent base of somewhat greater diameter than the mounting arm 35 to fasten within a chamber defined in an associated earplug for positional maintenance of the ear plug on the mounting arm.

Earplug 38 is a cone-like element having its base 39 laterally outermost and defining an innermost truncation 40 of hemispherical shape. The medial portion of the earplug defines of complimentary configuration chamber 41 to receive conic fastener 37 and the inner portion of mounting arm 35 for positional maintenance of the earplug on the mounting arm.

Preferably my safety glasses are formed of polymeric or resinous plastic material. The ball and socket joint elements require formation from some semi-rigid material that has resilient deformability to allow assemblage, but yet sufficient retentive memory to regain and maintain sufficient configurational integrity within a short period of time to allow insertion of the balls of ball and socket joints in their cooperating sockets. I have found known plastic materials such as polyvinyls, polypropylenes and the like to be suited for this purpose. Various of these plastic materials of a reasonably transparent nature and are therefore suitable for formation of the eye protector 42 and side protectors 44 so that those elements do not interfere with the vision of a user. Earplug 38 is preferably formed of foamed plastic material to provide user comfort during use and allow sufficient resilient deformation and retentive memory for fastening and positional maintenance on earplug mounting arm 35. This material deforms well into and fills the auditory canal of a user and may have sufficiently low sound transmissibility to prevent portions of sound waves externally of the auditory canal from entering that canal without substantial attenuation, if at all. Closed cell foamed type plastics commonly used for earplugs in the present day ear plugs are suited for use in my protection device.

For use of my protection device, safety glasses are formed according to the foregoing specification. By reason of the multiple joints in the device and the adjustments allowed thereby, such a protection device of configuration adapted for use by an average user may be well and comfortably adapted for use by a substantial range of somewhat differently sized and configured users. Preferably the various joints of the safety device are formed so that they have some frictional communication that allows manually activated motion of the joint, but yet provides some stable positional maintenance once a positional relationship of the joint parts is established.

Figure 4:
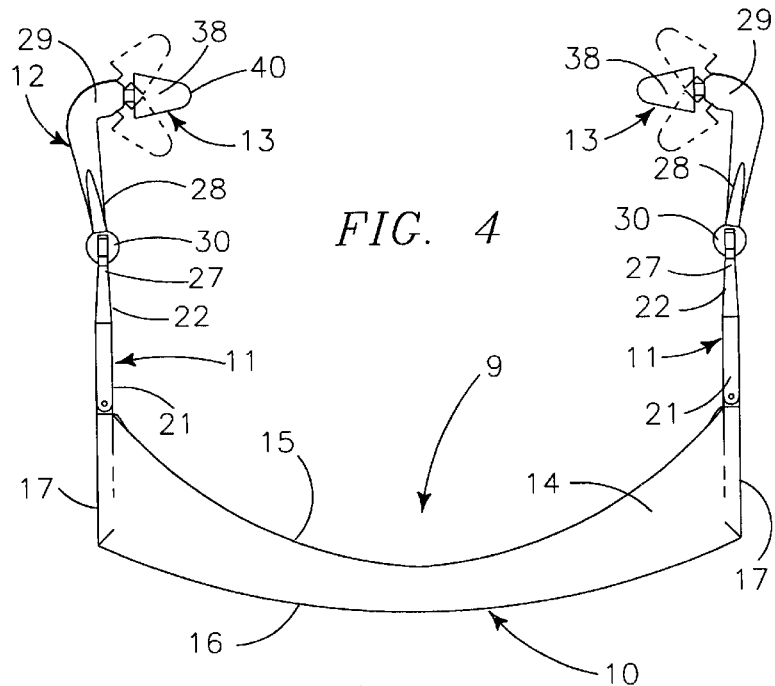
FIG. 4 is an orthographic top view of the protection device of FIG. 1 with the earplug structures shown in alternate positions in phantom outline.
Figure 3:
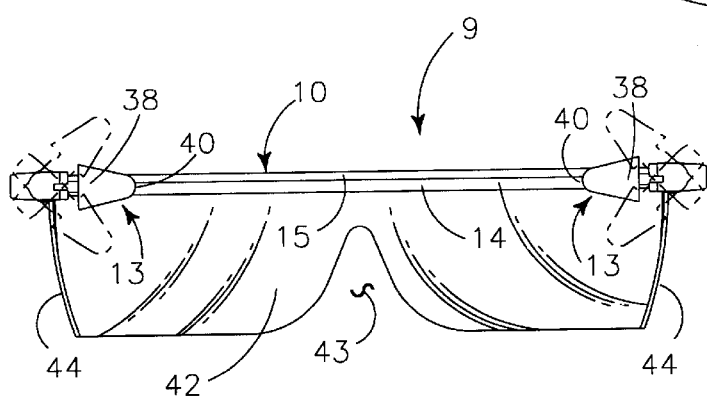
FIG. 3 is an orthographic front elevational view of the protective device of FIG. 1 with the earplug structures shown in alternate positions in phantom outline.
Figure 5:
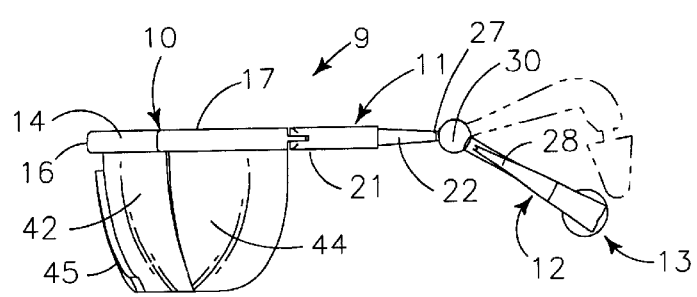
FIG. 5 is an orthographic left side elevational view of the protective device of FIG. 1 with the ear beam shown in phantom outline in an alternate position.

For use, the safety device is manually placed on the forehead of a user so that rearward surface 15 of forehead beam 10 is forwardly adjacent the user's forehead and the temple beams 11 and ear beams 12 extend rearwardly therefrom on each side of the user's head. If it be desired to simultaneously use the earplugs 38, each earplug is move to an inwardly extending position facing each other, as illustrated in solid outline in FIG. 4, and the ear beams 12 are adjusted to operatively position the earplugs in the user's auditory canals. If it not be desired to use the earplugs 38, the earplug structure 13 are folded forwardly as illustrated in phantom outline in FIG. 8 or 8A and the ear beams 12 are adjusted to fit in the space between the user's earlobes and the adjacent cranial structure. The various movable portions of the safety device then may be finely adjusted, if necessary, to provide the most comfortable fit of all parts for use.

The foregoing description of my invention is necessarily of a detailed nature so that a specific embodiment of its best mode may be set forth as required, but it is to be understood that various changes in detail, rearrangement and multiplication of parts might be resorted to without departing from its spirit, essence or scope.

Having thusly described my invention, what I desire to protect by utility Letters Patent, and

What I claim is:

1. An eyes and ears protection device comprising in combination:

safety glasses having a forehead beam supporting a depending eyes shield, said forehead beam having lateral ends and articulately carrying temple beams at each lateral end for pivotal motion in a horizontal plane to extend rearwardly on each lateral side of the head of the user, each temple beam articulately carrying a rearwardly extending ear beam for limited universal motion in three mutually perpendicular planes, each ear beam articulately carrying an ear plug structure for limited universal motion in three mutually perpendicular planes.

2. The protection device of claim 1 having side protectors depending from each lateral end of the forehead beam and extending spacedly rearwardly from the eyes shield.

3. The protection device of claim 1 wherein the temple beam articulately carries the ear beam by a ball and socket joint formed therebetween.

4. The protection device of claim 1 wherein the ear beam articulately carries the ear plug structure by a ball and socket joint formed therebetween.

5. The protection device of claim 1 wherein the ear plug structure comprises an ear plug mounting arm having means for interconnecting the ear beam at a first end and carrying a resiliently deformable configurationally sustaining truncated conical ear plug at a second end.

6. The protection device of claim 1 wherein the ear beam is an L-shaped member formed by a forward elongate portion having means at a first forward end to articulately interconnect the temple beam and a laterally inwardly extending rearward portion articulately carrying the ear plug structure at a second inward end.

7. The protection device of claim 6 wherein the ear beam defines an indentation to partially contain the ear plug structure carried thereby when the ear plug structure is positioned to extend elongately forwardly.

8. An eyes and ears protection device comprising in combination:

safety glasses having a forehead beam, with similar opposed lateral ends, supporting a forward depending eyes protector and similar opposed depending side protectors extending rearwardly from the eye protector, said forehead beam articulately carrying at each lateral end, for pivotal motion in a horizontal plane, similar temple beams to extend rearwardly on each lateral side of the head of a user, each temple beam articulately carrying a rearwardly extending ear beam by a ball and socket joint defined between the temple beam and the ear beam for limited universal motion in three mutually perpendicular planes, each said ear beam comprising an L-shaped member formed by a elongate forward portion and a laterally inwardly extending rearward portion defining an indentation therein to partially contain an ear plug, each ear beam articulately carrying a rearwardly extending ear plug structure by a ball and socket joint defined therebetween for limited universal motion in three mutually perpendicular planes, said ear plug structure articulately carrying an ear plug mounting arm at a first end for limited universal motion in three mutually perpendicular planes, said ear plug mounting arm carrying a resiliently deformable configurationally sustaining truncated conical ear plug at a second end.

\* \* \* \* \*